United States Patent [19]

Tomatis

[11] 4,212,119
[45] Jul. 15, 1980

[54] AUDIO-VOCAL INTEGRATOR APPARATUS

[75] Inventor: Ange A. A. Tomatis, 68 Bd de Courcelles, 75017 Paris, France

[73] Assignee: Ange Alfred Auguste Tomatis, Paris, France

[21] Appl. No.: 940,208

[22] Filed: Sep. 7, 1978

[30] Foreign Application Priority Data

Jul. 19, 1978 [FR] France .................................. 78 21407

[51] Int. Cl.³ ...................... G09B 19/04; H04R 3/00
[52] U.S. Cl. ..................................... 35/35 C; 179/1 N
[58] Field of Search ..................... 35/1, 35 C, 8 A, 13; 179/1 N

[56] References Cited

U.S. PATENT DOCUMENTS

| 3,101,081 | 8/1963 | Tomatis | 35/35 C |
| 3,358,390 | 12/1967 | Korn | 35/35 C |
| 3,373,508 | 3/1968 | Holden et al. | 35/35 C |
| 3,561,138 | 2/1971 | Catlin et al. | 179/1 N |
| 3,949,735 | 4/1976 | Klar et al. | 179/1 N |
| 4,021,611 | 5/1977 | Tomatis | 179/1 N |

FOREIGN PATENT DOCUMENTS 2260153 8/1975 France .................................. 35/35 C Primary Examiner—Vance Y. Hum
Attorney, Agent, or Firm—J. Harold Nissen

[57] ABSTRACT

An audio-vocal integrator apparatus to develop the listening and language functions of a subject. The ear of the subject is alerted to an acoustical signal by osseous conduction and the signal is only transmitted to the ear after the ear has been previously alerted by osseous conduction.

5 Claims, 1 Drawing Figure

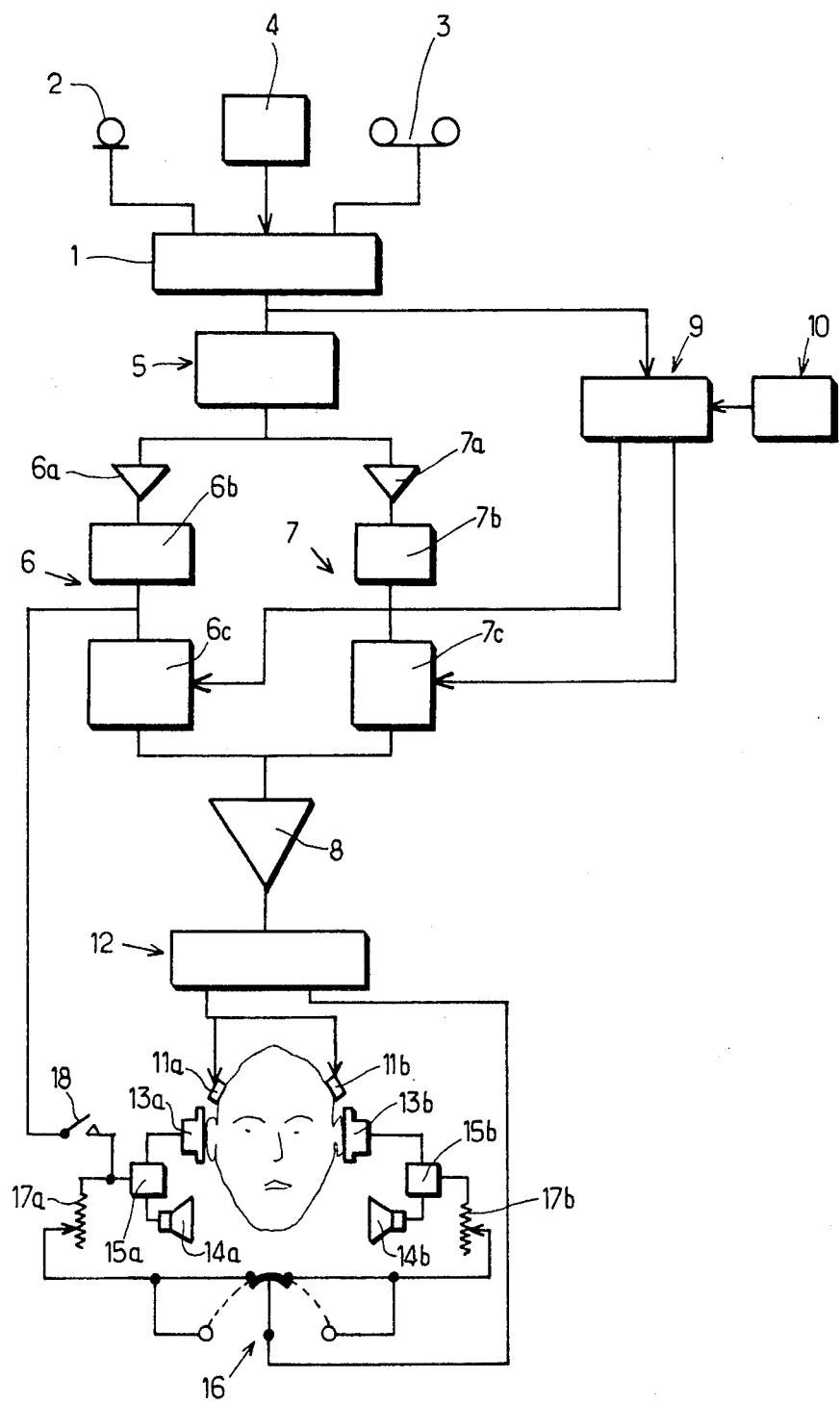

AUDIO-VOCAL INTEGRATOR APPARATUS

BACKGROUND OF THE INVENTION

The present invention relates to an audio-vocal integrator apparatus, i.e. an apparatus which enables a good development of the function of listening of a subject to be obtained, and, correlatively, the functions of the language which logically follow therefrom to be aroused.

According to the so-called "Tomatis" effect and as consequence of this effect, it is known that any modification in the auditive supply applied to a subject, i.e. in the sound information which he/she receives, induces a transformation of his/her vocal supply, i.e. of the physical characteristics of the sound message which he/she emits by speaking or singing. This verified and easily verifiable fact requires, however, particular conditions to be, on the one hand, faithfully realised and, on the other hand, memorised and reproduced with the same fidelity, i.e. to some extent to be integrated and fully restituted. It is readily appreciated that these conditions may be established only from a particular knowledge of the mechanisms of hearing.

It is presently known that the ear is already operational in its vestibular functions of balance and cochlear functions of hearing in the uterus. Thus, the ear is essentially built, as demonstrated by phylogenesis, on the mode of perception in an aquatic medium. Its subsequent problem, when the baby is born, is then centred on the fact that it must pass from hearing in an aquatic medium to hearing in an aerial medium and that, consequently, it must adapt itself to this aerial hearing. This new adaptation can only be effected as a function of what was acquired whilst in the uterus, i.e. based on the mechanisms of the inner ear itself bathing in a liquid medium both surrounding it and contained in its own inner structure.

Thus, to understand and possibly start the adaptation of the ear to aerial hearing, it is necessary to aid the middle and outer ear to organise themselves with a view to this new perception. To this end, the conditions required are often difficult to totalize, as the influences of all types, such as emotional, family, social and cultural, risk hindering the process of adaptation.

SUMMARY OF THE INVENTION

It is an object of the present invention to provide an apparatus which will enable the ear of a subject to benefit from this mechanism of adaptation and therefore arouse the functions of language which obviously follow from the good development of the listening function.

To this end, this audiovocal integrator apparatus, comprising an input stage connected to at least one source of sound such as a microphone, tape recorder, etc. . ., an output stage supplying electro-acoustic transducers emitting sounds applied by the aerial route to the ears of a subject, a pair of main channels connected in parallel between the input and output stages and each comprising, in series, a filter and a gate controlling the opening or closure of the main channel in question, and an auxiliary control channel connected to the output of the input stage and connected to the two gates of the two main channels to open and close these two main channels, alternately and automatically, as a function of the level of the signal at the output of the input stage, and at least one vibrator for converting an electric signal into vibrations applied to part of the skin or bone of the subject to ensure a conduction of osseous route, is characterised in that means are provided to transmit, upon each train of electric signals corresponding to a sound signal applied to the input stage, the signal appearing at the output of the output stage, firstly solely to the or each vibrator ensuring a conduction of the osseous route and then, after a predetermined delay, solely or also to the or each electroacoustic transducer ensuring the conduction by the aerial route.

The apparatus according to the invention thus makes it possible, upon the emission of each train of sound signals, to actuate first the or each vibrator which thus brings the inner ear in listening posture identical to that by which it is originally engaged upon conduction by the osseous route. It is only a certain time afterwards that the electroacoustic transducers such as earphones, loud-speakers, which ensure conduction by the aerial route, become in turn operational to impose aerial conduction on the inner ear.

The apparatus according to the invention thus enables the passage from hearing by the osseous route to hearing by the aerial to be repeated a large number of times, until this pnenomenon is totally integrated.

Under these conditions, due to the use of the apparatus according to the invention, reponses which are as good as possible are obtained of the phonation which itself becomes, further to the vocal counter-reaction conducted by the microphone, a source of sounds particularly selected to provoke this phenomenom of adaptation since at the same time as the ear is adapting itself the process of phonation becomes the actual generator of the process of adaptation. After education to this phenomenon and incessant repetition of this latter, the whole will eventually be able to be continued spontaneously, hence the total integration of the phenomenon. The apparatus according to the invention proves particularly adapted to all education concerning listening and lauguage, namely:

from the pedagogic point of view: school (school groups), lauguages (modern languages), singing, music;

from the psychological point of view, by reestablishing the desire to listen and resuming the relational processes;

from the medical point of view: for releasing blockages, source of somatization;

from the psychiatric point of view, by bringing the subjects away from narcissic speech and by reestablishing listening with the social environment.

BRIEF DESCRIPTION OF THE DRAWINGS

The invention will be more readily understood on reading the following description of an embodiment thereof, with reference to the accompanying drawings, in which:

DESCRIPTION OF THE PREFERRED EMBODIMENT

The single FIGURE shows a block diagram of an audiovocal integrator apparatus according to the invention.

Referring now to the drawing, the apparatus according to the invention comprises an input stage 1 to which may be connected one or more external sound sources such as a microphone 2, or a tape recorder 3 with recorded tapes, music or mother's voice, or a record player with discs, or a sound generator 4, which source may be actuated by any desired sources.

The input stage 1 which receives at its input the electric signal coming from the selected source, for example the microphonic signal coming from microphone 2, emits at its output a suitably amplified signal which is applied to the input of a chain of filters 5. These filters may automatically or manually scan the frequency band ranging from zero to 12,000 Hz and vice-versa to effect the different adaptations of the sound signal emitted by the source, according to the application envisaged.

The output of the filter 5 is connected to the input of two main channels generally designated as a whole by references 6 and 7 respectively, these two channels extending between the input stage 5 and an output stage shown schematically by a power amplifier 8. The two main channels 6,7 successively comprise input amplifiers 6a, 7a, filters 6b, 7b, and gates 6c, 7c. The response curve of the filters 6b, 7b, is adjustable and selected as a function of the purpose of the apparatus. This response curve may be modified as desired according to the application envisaged. The first channel 6 or rest channel comprises a filter 6b preferably ensuring the total relaxation of the inner ear and consequently essentially presenting the characteristic of a low-pass filter. The characteristic of the filter 7b of the second channel 7 may be adjusted as desired by means of knobs for adjusting the apparatus, acting on potentiometers, capacitors or variable inductors.

The apparatus according to the invention further comprises an auxiliary control channel 9 which is constituted, in manner known per se, by a threshold circuit controlling a monostable or bistable flip flop which is in rest position in the absence of signal at the output of the input stage 2. In this stage, the control channel 9 emits, on its outputs, signals which, applied to the gates 6c, 7c, provoke the opening of gate 6c of the first main channel 6 and the closure of gate 7c of the second main channel 7. Under these conditions, in the rest state, the signals applied to the input stage 1 are transmitted through the first main rest channel 6 as far as the output power amplifier 8 to be amplified thereby.

As soon as the level of the signal applied to the input stage 1 reaches a predetermined threshold (for example as soon as the subject speaks into the microphone 2), the level of the signal at the output of the input stage 1 rises and provokes the tipping of the control channel 9. This latter then determines the closure of the gate 6c, and, on the contrary, the opening of the gate 7c. From this moment, the second main working channel 7 is switched on and the electric signals are transmitted through this second channel and particularly through filter 7b, to be applied thereafter to the output power amplifier 8.

As was seen previously, the first channel 6 enables the inner ear to be fixed in a state of maximum non-adaptation or of relaxation whilst the second channel 7 fixes the ear in a chosen state of maximum or optimal adaptation. The passage of the first channel 6 towards the second channel 7 must be effected so that the intensity of the first channel 6 is always equal to the intensity of the second channel 7 at all moments of the operation. In other words, there is no modification of the level of intensity which must remain identical. Only, of course, the frequency field changes, due to the replacement of the filter 6b by filter 7b. This is a conversion of the overall information and not a simple filtering.

The output signals emitted by the apparatus according to the invention may be applied to vibrators placed at suitable spots on the skin or bones of the suject, for example in contact with the mastoid bones, slightly behind each ear. The two right-hand and left-hand vibrators 11a and 11b are connected to a first output of a delay output circuit generally designated by 12. This circuit further comprises a second output which is connected to ear-phones 13a, 13b placed on the subject's ears, and also to loud-speakers 14a, 14b. The ear-phone 13a and loud-speaker 14a are located to the right of the subject whilst the ear-phone 13b and the loud-speaker 14b are placed on the left.

The output delay circuit 12 is designed so as to introduce a determined delay between the energisation of the vibrators 11a, 11b, which takes place immediatly, as soon as a signal appears at the output of the power amplifier 8, and that of the electroacoustic transducers which are constituted by the ear-phones 13a, 13b, and the loud-speakers 14a, 14b. This delay may be between 0.03 and 0.10 seconds.

Thus, when a sound message in the form of electric signals is applied to the output of the apparatus, this message is transmitted in the first place to the vibrators 11a, 11b, which act alone, in a first stage, to bring the inner ear in a listening posture identical to that by which it was originally engaged. After a short period of time has elapsed, corresponding to the above-mentioned delay, the sound message is emitted on the second output of the circuit 12 and is applied to the ear-phones 13a, 13b or loud-speakers 14a, 14b which thus in turn become operational. During this time, the vibrators 11a, 11b may be maintained in the operational state or may be switched off.

Means may of course be provided to vary the length of the delay in the circuit 12, according to need.

Switching circuits 15a, 15b are provided to switch on the ear-phones 13a, 13b and/or the loud-speakers 14a, 14b, as desired.

A switch 16 may be provided to switch on either the members located to the left, 13a, 14a, or the members located on the right, 13b, 14b, or all of time, selectively. Rheostats 17a, 17b may be connected so as to adjust the respective levels of the signals applied to the ear-phones and/or loud speakers.

A switch 18, normally open, is additionally provided to possibly connect one of the ear-phones and/or loud speakers to the output of the filter 6b of the first channel 6. In the present case, if the switch 18 is closed, the right-hand ear-phone 13a and/or the right-hand loud speaker 14a permanently receives the signals passing in the first channel 6. In this case, the switch 16 is placed in the position in which the output circuit 12 supplies solely the left-hand ear-phone 13b and/or the left-hand loud speaker 14b, i.e. in the right-hand position in the drawing. Any other combination of the phenomena of tipping between the two channels may of course be provided.

What we claim is:

1. An audiovocal integrator apparatus, comprising an input stage connected to at least one source of sound; an output stage having electroacoustic transducers emitting sounds applied by the aerial route to the ears of a subject; a pair of main channels connected in parallel between the input and output stages and each comprising, in series, a filter and a gate controlling the opening or closure of the main channel in question, and an auxiliary control channel connected to the output of the input stage and connected to the two gates of the two main channels to open and close these two main channels alternately and automatically, as a function of the level of the signal at the output of the input stage, and at least one vibrator for converting an electric signal into vibrations applied to a part of the skin or bone of the subject to ensure a conduction by the osseous route; and means for transmitting, upon each train of electric signals corresponding to a sound signal applied to the input stage, the signal appearing at the output of the output stage, firstly solely to the vibrator ensuring a conduction by the osseous route and thereafter, after a predetermined delay, solely or also to the electroacoustic transducers ensuring the conduction of the aerial route, including a delay circuit having two outputs of which one, where the input signal transmitted without delay appears, is connected to the vibrator and the other, where the input signal appears after a predetermined delay, is connected to the electroacoustic transducers.

2. An apparatus as claimed in claim 1, wherein it comprises a switch for selectively switching on the electroacoustic transducers located to the right and/or left of the subject.

3. An apparatus as claimed in claim 1, wherein means are provided to regulate the intensity of the current energizing the electroacoustic transducers.

4. An apparatus as claimed in claim 1, wherein means are provided to maintain one or more of the electroacoustic transducers permanently connected to the output of the filter of the first main channel.

5. An audiovocal integrator apparatus, comprising means for producing an acoustical signal; means for alerting the human ear by osseous conduction to the imminence of an acoustical signal; and means for transmitting the acoustical signal to the ear only after the ear has been alerted previously by osseous conduction.

* * * * *

UNITED STATES PATENT AND TRADEMARK OFFICE
CERTIFICATE OF CORRECTION

PATENT NO. : 4,212,119
DATED : July 15, 1980
INVENTOR(S) : Ange A. A. Tomatis

It is certified that error appears in the above—identified patent and that said Letters Patent is hereby corrected as shown below:

Column 2, Line 27  correct the spelling of "responses"

Column 4, Line 42  "time" should be --them--

Signed and Sealed this

Eleventh Day of November 1980

[SEAL]

Attest:

SIDNEY A. DIAMOND

Attesting Officer

Commissioner of Patents and Trademarks